United States Patent [19]
Dastur et al.

[11] Patent Number: 5,772,635
[45] Date of Patent: Jun. 30, 1998

[54] AUTOMATED INFUSION SYSTEM WITH DOSE RATE CALCULATOR

[75] Inventors: Kamal M. Dastur, Los Angeles; Paul A. Koenig, San Diego; Gary Werschmidt, Yorba Linda; Son Hong, El Monte; Jack Jiang, San Diego, all of Calif.

[73] Assignee: ALARIS Medical Systems, Inc., San Diego, Calif.

[21] Appl. No.: 440,871

[22] Filed: May 15, 1995

[51] Int. Cl.⁶ .................................................. A61M 31/00
[52] U.S. Cl. ............................................. 604/131; 604/67
[58] Field of Search .............................. 604/131, 65, 66, 604/67; 128/DIG. 12, DIG. 13

[56] References Cited

U.S. PATENT DOCUMENTS

| | | | |
|---|---|---|---|
| 3,654,445 | 4/1972 | Mikkelsen et al. | 235/151.3 |
| 4,308,866 | 1/1982 | Jelliffe et al. | 128/214 E |
| 4,551,134 | 11/1985 | Slavik et al. | 604/67 |
| 4,553,958 | 11/1985 | LeCocq | 604/67 |
| 4,560,979 | 12/1985 | Rosskopf | 604/131 X |
| 4,696,671 | 9/1987 | Epstein et al. | 604/67 |
| 4,710,166 | 12/1987 | Thompson et al. | 604/65 X |
| 4,741,732 | 5/1988 | Crankshaw et al. | 604/67 X |
| 4,756,706 | 7/1988 | Kerns et al. | 604/66 |
| 4,807,170 | 2/1989 | Kulli et al. | 264/413.01 |
| 4,850,972 | 7/1989 | Schulman et al. | 604/151 |
| 4,898,578 | 2/1990 | Rubalcaba, Jr. | 604/66 |
| 4,943,279 | 7/1990 | Samiotes et al. | 604/151 |
| 4,946,439 | 8/1990 | Eggers | 604/67 |
| 5,009,641 | 4/1991 | Gorton | 604/131 |
| 5,041,086 | 8/1991 | Koenig et al. | 604/65 |
| 5,088,981 | 2/1992 | Howson et al. | 604/31 |
| 5,104,374 | 4/1992 | Bishko et al. | 604/31 |
| 5,153,827 | 10/1992 | Coutré et al. | 364/413.02 |
| 5,219,330 | 6/1993 | Bollish et al. | 604/53 |
| 5,256,157 | 10/1993 | Samiotes et al. | 604/246 |
| 5,295,967 | 3/1994 | Rondelet et al. | 604/67 X |
| 5,376,070 | 12/1994 | Purvis et al. | 604/31 |
| 5,382,232 | 1/1995 | Hague et al. | 604/65 |
| 5,507,412 | 4/1996 | Ebert et al. | 604/67 X |

OTHER PUBLICATIONS

International Search Report in International Application No. PCT/US96/06945; dated Jul. 12, 1996.

*Primary Examiner*—Sam Rimell
*Attorney, Agent, or Firm*—Fulwider Patton Lee & Utecht, LLP

[57] ABSTRACT

A medication infusion system having an integrated dose rate calculation feature for selectively assigning values to a plurality of infusion parameters and automatically calculating an infusion rate from the selected parameters. One embodiment includes a stored list of drug names having associated dose rate and concentration units that are automatically set when a drug name is selected from the list. Another embodiment includes "Fast" softkeys that can be programmed to display parameter values or drug names in a predetermined sequence. The dose rate calculation feature may also be used during infusion to titrate the dosage being delivered to the patient for improved therapeutic results. The stored list of drug names and associated infusion parameters may be altered by qualified personnel using an external programming source running specialized software.

33 Claims, 4 Drawing Sheets

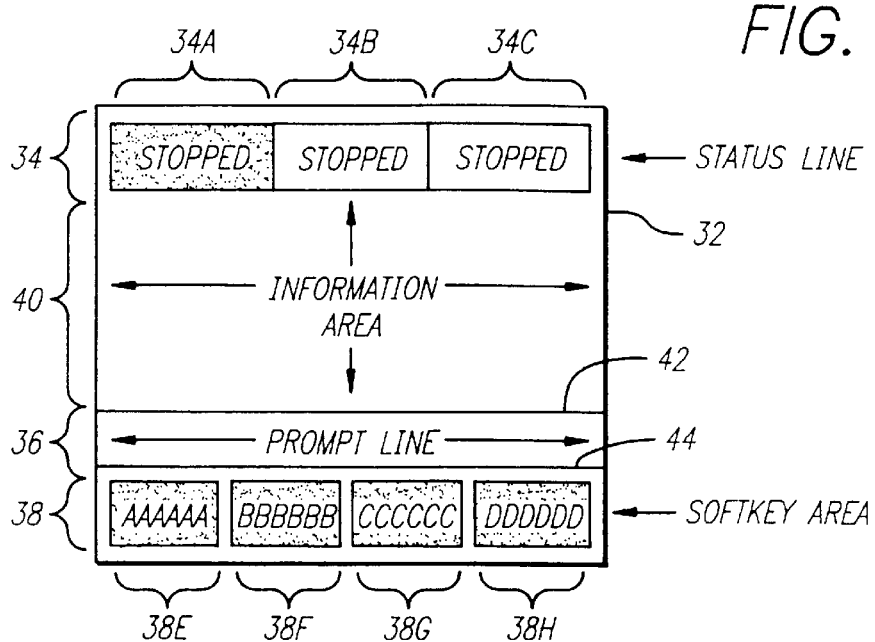
FIG. 3
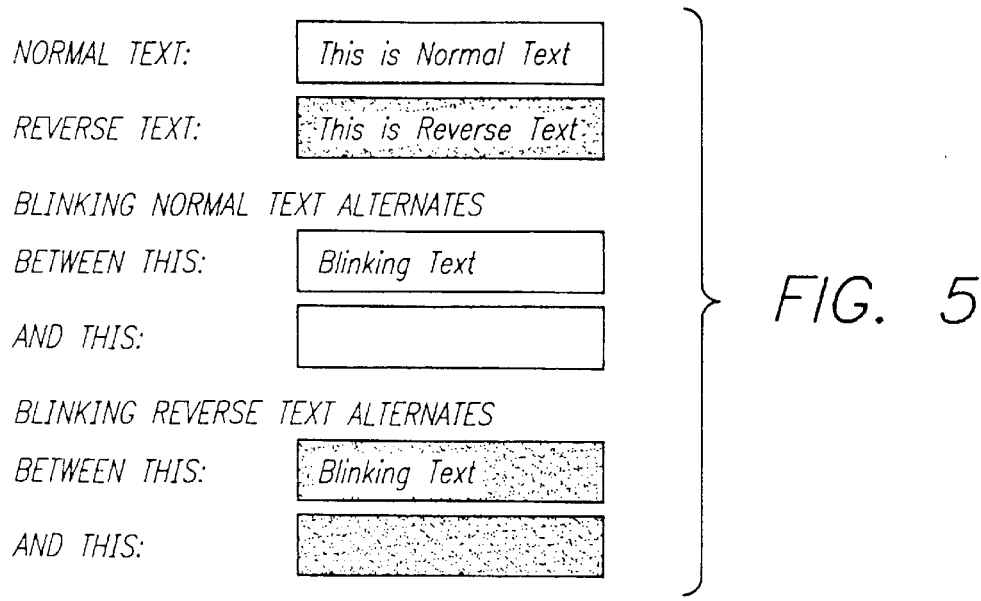
FIG. 4
FIG. 5

FIG. 8

```
A: STOPPED

A: PRIMARY RATE:      7.0 ml/h
A: PRI VOL REM (VR):  100.0 ml/h
A: PRI TIME (TR):       14h 17m
A: PRI VOL INF:           0.0 ml

SINCE 11:13a 13 JUN 94
─────────────────────────────────
   PRESS SELECT TO CHOOSE LINE
  [     ] [2°SEC] [     ] [CALC.ON]
```

FIG. 9

```
A: STOPPED
[DRUG?] Wt. --
A: CONC-------mg/------ml
A: DOSE-------mcg/kg/min
A: RATE-------ml/h
A: VR           1.0 ml (Vol Rem)

A:VI   0.0 ml   DI   0.0 mg
[SELECT] [↑] [↓] [FAST↑]
```

AUTOMATED INFUSION SYSTEM WITH DOSE RATE CALCULATOR

BACKGROUND OF THE INVENTION

1. Field of the Invention

The present invention relates generally to systems for continuously infusing medication into a patient and, more particularly, to infusion pumps providing an integrated dose rate calculation function.

2. Description of the Related Art

A relatively recent apparatus for administering medication to a patient is the medication infusion pump. A valuable and much needed development, the medication infusion pump can be used to administer drugs to a patient in small, carefully measured doses at frequent intervals or, with some devices, slowly but uninterruptedly. A therapeutic regimen with an infusion pump can be controlled electronically to administer precisely measured quantities of a drug at precisely planned intervals to give a gradual infusion of medication into the patient. The infusion pump makes possible a closer approximation to the natural maintenance of biochemical balances in the body because of its operation in a repetitive small dose mode.

As availability of drugs, therapeutic techniques, and technological capability have improved, the demand for sophistication in drug delivery has increased. In many instances, this added sophistication results in more complicated infusion pump operation. Achieving this sophistication in drug delivery capability, and maintaining ease of use has been a major challenge for infusion pump manufacturers.

As the sophistication of the available infusion pumps has increased, so too have the number of parameters that may be used to control the infusion. Typically, an infusion pump comprises a pumping element that causes a precisely measured flow of fluid to be infused to the patient. This pump element is controlled by a processor that generally has a programmable memory associated with it for storing instructions to be used by the processor to control the infusion. The sophistication of currently available infusion pumps with programmable processors and extensive memory capabilities for controlling complicated drug delivery schemes adds significantly to the choices available to a physician for prescribing a drug regimen to be infused.

The range of possible infusion parameters includes, but is not limited to, infusion rate, infusion duration, dose volume, lockout period, repeat period, bolus size and bolus rate, patient weight, syringe size, container volume, security codes, drug units (e.g. milligrams), drug concentration, concentration units or pharmacokinetic parameters. Each of these parameters may be entered by a user into the memory of the pump using a keyboard connected directly to the pump. Alternatively, the pump may be programmed by commands received over a network or other communication scheme from a central computer.

Because of the large number of therapeutic modalities and the extensive number of possible required parameters, the manufacturers have been challenged to provide a user interface that assists the user in entering desired parameters by simplifying the entry process as much as possible. For example, there is a need for a user interface that automatically selects as many secondary parameters as possible that are associated with a particular primary infusion parameter. For example, it would be useful to provide a user with predetermined ranges of parameter values depending on the type of drug to be infused.

The infusion device industry has collectively responded to these needs in a number of ways. First, compromises in features are often accepted in the interest of having versatile, general or multi-purpose pumps. For example, physicians may sometimes select doses based on body weight and drug units, but the pumps are not capable of being programmed without first converting those values to other values that are acceptable to the processor of the pump. For example, when necessary, users must manually perform conversion calculations so that rates may be programmed in ml/hr, although the dose was prescribed in mcg/kg/day. These calculations consume large amounts of valuable user time, and require extra time to check for accuracy both after calculation and when they are entered into the pump.

Determining the parameters to be programmed into an infusion pump typically proceeds in one of two ways. In what may be called dosage-based operation, the physician specifies a dosage to be administered. The corresponding infusion rate must then be calculated so that the infusion pump can be controlled accordingly. In volumetric rate-based operation, however, there is no need to calculate the infusion rate because it is specified by the processor. Instead, volumetric rate-based operation involves calculation of the corresponding dosage of the drug, this being done so that a record may be kept of the dosage of the drug that is administered to the patient.

In either case, a calculation must be made, and it is therefore desirable that the system include some means for doing this in a manner that simplifies the task as much as possible, and in so doing, also assists the user by improving the accuracy of the calculation and easing the programming of the calculated parameter into the memory of the pump. The calculation procedure should be quick and convenient with little chance for user confusion and error, and it should facilitate medication adjustments according to patient reaction.

Stand-alone calculators to perform the conversion of infusion parameters as described above exist; however, they still require entry of the calculated value into the memory of the pump. These calculators, for example, typically require the specified dosage or infusion rate to be entered along with other necessary parameter values. Then, the solution to the calculation, either infusion rate or dosage, is displayed. This value must then be transferred to the corresponding infusion pump, with the process taking time and effort and risking that a parameter will be inaccurately transferred to the infusion pump.

Another approach to this problem has been to connect individual infusion pumps to a computer network that has a program available to assist the technician with the dosage calculations. In operation, the nurse or technician accesses the computer network from a terminal or workstation located at a nurse station or at the patient's bedside. The nurse or technician enters the parameters for the infusion prescribed by the physician, and the specialized drug calculation program performs the required calculations. When the nurse or technician is satisfied, he or she may request that the entered and calculated parameters be downloaded through the computer network into the infusion pump.

Centralized calculation programs of the sort described above can be quite powerful, providing, in addition to a dosage calculation program, a checking function to cross-reference with the patient records to detect an inappropriate infusion parameter. It may also maintain a database of drug information that can be cross-checked with the patient's medical history to determine whether a drug has been prescribed that may elicit an allergic reaction by the patient if it is infused. One example of such a centralized system also maintains a list of typical drugs infused, along with typical default concentration and dose units. This system allows for more rapid and error free calculation by providing the technician with a list of commonly infused drugs to select from. Selection of a drug from the list automatically enters default dose units and infusion parameters.

A problem with such centralized computer systems is that they typically require specialized hardware, software, and network wiring and interfaces that may be expensive to install and to maintain. Where such centralized systems are not available, care providers may rely on stand-alone calculators, as previously described, to perform the necessary calculations to covert dosage parameters to volumetric rate parameters acceptable to the infusion pumps in their institution. One approach to meeting the need of such care givers for a pump having a dose rate calculator has been described by Rubalcaba in U.S. Pat. No. 4,898,578. This patent discloses an infusion system having an integral dose rate calculator that provides an operator with a menu of infusion related parameters. Values for infusion rate, dosage per unit of body weight per unit of time or dosage per unit of time, body weight, volume of solution and weight of the drug may be entered. In operation, the technician must enter four of the above five parameters and the calculator determines the remaining parameter. This infusion system, however, still requires the user to enter a large number of infusion parameters, including dosage units and concentration units.

What has been needed, and heretofore unavailable, is an infusion pump having a dose rate calculation feature that allows an operator to quickly and accurately program the pump by selecting the name of a desired drug from a list of drugs stored in the memory of the pump. Selecting such a name should also automatically select default parameters for the most commonly used dose units and drug concentrations. This would reduce the number of parameters to be entered by the user, improving accuracy and reducing the time needed to perform the calculation. Additionally, such a system would eliminate the need for a user to transfer the infusion parameters to the pump prior to beginning infusion.

Also needed is a fast and accurate way to select a drug name from a list of drug names where such a selection also programs the pump with default values for various infusion parameters, such as the typical concentration used within the care giving facility for a particular drug, associated dose units and concentration units. In many institutions, a relatively limited number of different types of drugs are routinely prescribed. Often, the institution's pharmacy will stock only a selected range of concentrations of these drugs to minimize the amount of inventory that must be maintained to reduce costs and the potential for a drug to stay on the pharmacy's shelf past its expiration date. Thus, further improvements in ease of use, accuracy, and time savings may result if the concentrations of this select group of drugs could be programmed into the pump, so that selection of the drug by name automatically programs the standard value of the concentration into the pump for use during the dose rate calculation process. Even more useful would be an infusion pump having a memory that can be altered using an external programming source to add, remove or update the stored lists of drug names and associated infusion parameters. The present invention meets these needs.

SUMMARY OF THE INVENTION

Briefly, and in general terms, the invention is directed to an infusion pump having a memory in which is stored a list of drug names, each name also having a group of infusion parameters associated with the name, so that a user may select a name from the list of drug names and thereby automatically enter appropriate values for dosage and concentration units. The pump also provides a user interface for selecting values from stored ranges of values of other required infusion parameters, automatically converting entered values to other values, for example, patient weight in kilograms to pounds, and pounds to kilograms, and for automatically calculating volumetric infusion rate from parameters prescribed and entered in dosage units.

In another aspect, the pump also displays software dependent "fast keys" that are used for scrolling through a list of drug names, jumping from one predetermined drug name to another predetermined drug name for rapidly moving through the list of drug names and speeding the selection of the desired drug name from the list.

In a further aspect, the infusion pump allows the user to modify selected infusion parameters during the infusion to adjust for patient response to the drug regimen. Entry of the selected parameters results in a recalculation of the dosage or infusion rate, with the new values being displayed on the pump for the users convenience.

In yet another aspect, the memory of the infusion pump containing the stored lists of drug names and associated infusion parameter values may be altered by connecting the infusion pump to an external programming source running specialized software via a communication interface. In this manner of operation, an institution may customize the list of drug names and associated infusion parameters, programming each infusion pump to meet specific needs.

BRIEF DESCRIPTION OF THE DRAWINGS

FIG. 3 is a schematic diagram of a layout of a display of the user interface display device of FIG. 2.

FIG. 4 shows the font definitions for the liquid crystal display of FIG. 3.

FIG. 5 shows the text display attributes for the liquid crystal display of FIG. 3.

FIG. 8 is an example of the display showing a channel information page and the infusion parameters that may be selected by a user to program the infusion pump when the pump is operating in a volumetric mode;

FIG. 9 is an example of the display showing the channel information page displayed when the pump is operating in a Dose Rate Calculation mode, including a drug name and other infusion parameters that may be selected by a user to program the infusion pump; and

DETAILED DESCRIPTION OF THE PREFERRED EMBODIMENTS

Figure 1:
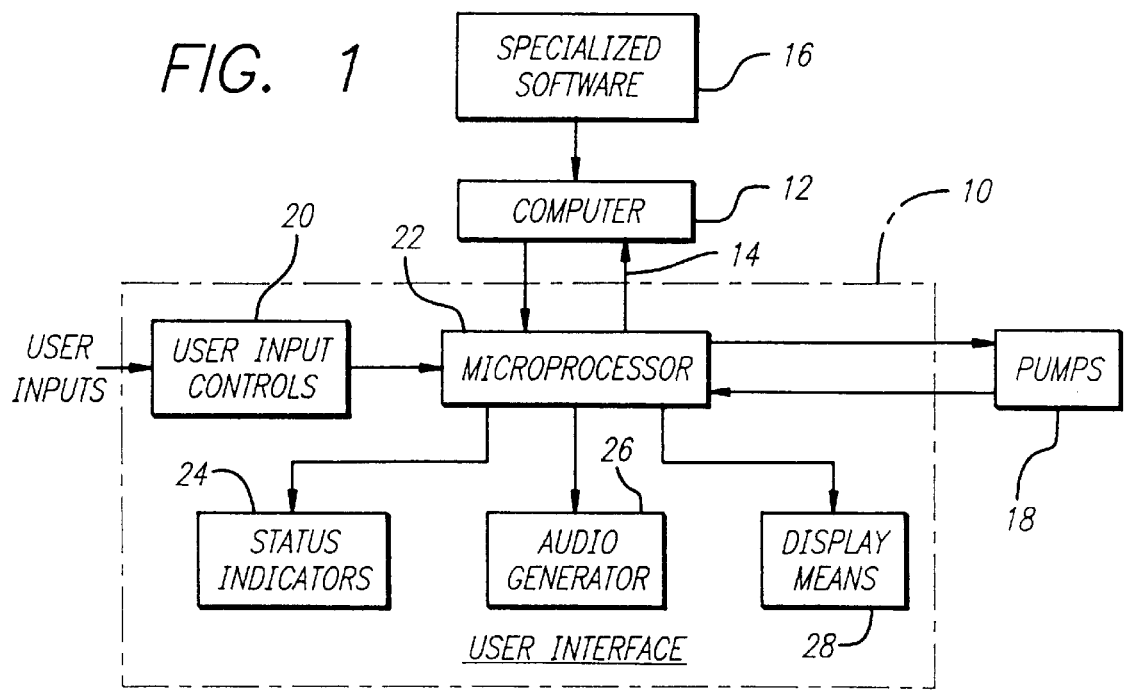
FIG. 1 is a schematic block diagram of a user interface in a multimode medical infusion system.

Referring now to the drawings in more detail in which like numerals correspond to like or similar details of the apparatus depicted, FIG. 1 shows a schematic block diagram of a user interface for a multimode medication infusion system. The user interface 10 is able to communicate with an off-line digital computer 12 via communications interface 14. When the user interface 10 is connected to the computer 12 in this way, specialized software 16 may be run on the computer 12 to enable selected qualified personnel to change default values for various parameters associated with operation of the medication infusion system. This mode of operation of user interface 10 is called the "maintenance mode" and will be discussed more fully below.

Normally the user interface 10 is not connected to the computer 12. The user interface 10 controls the functioning of a medication infusion system employing a disposable fluid pathway that incorporates a sterile cassette 18 containing pumping elements and sensor interfaces in a multi-channel configuration, as described in U.S. Pat. No. 4,919,596, entitled "Fluid Delivery Control and Monitoring Apparatus for a Medication Infusion System," assigned to the assignee of this application.

The user interface 10 comprises user input controls 20, a microprocessor 22, status indicators 24, an audio generator 26, and a display 28.

Figure 2:
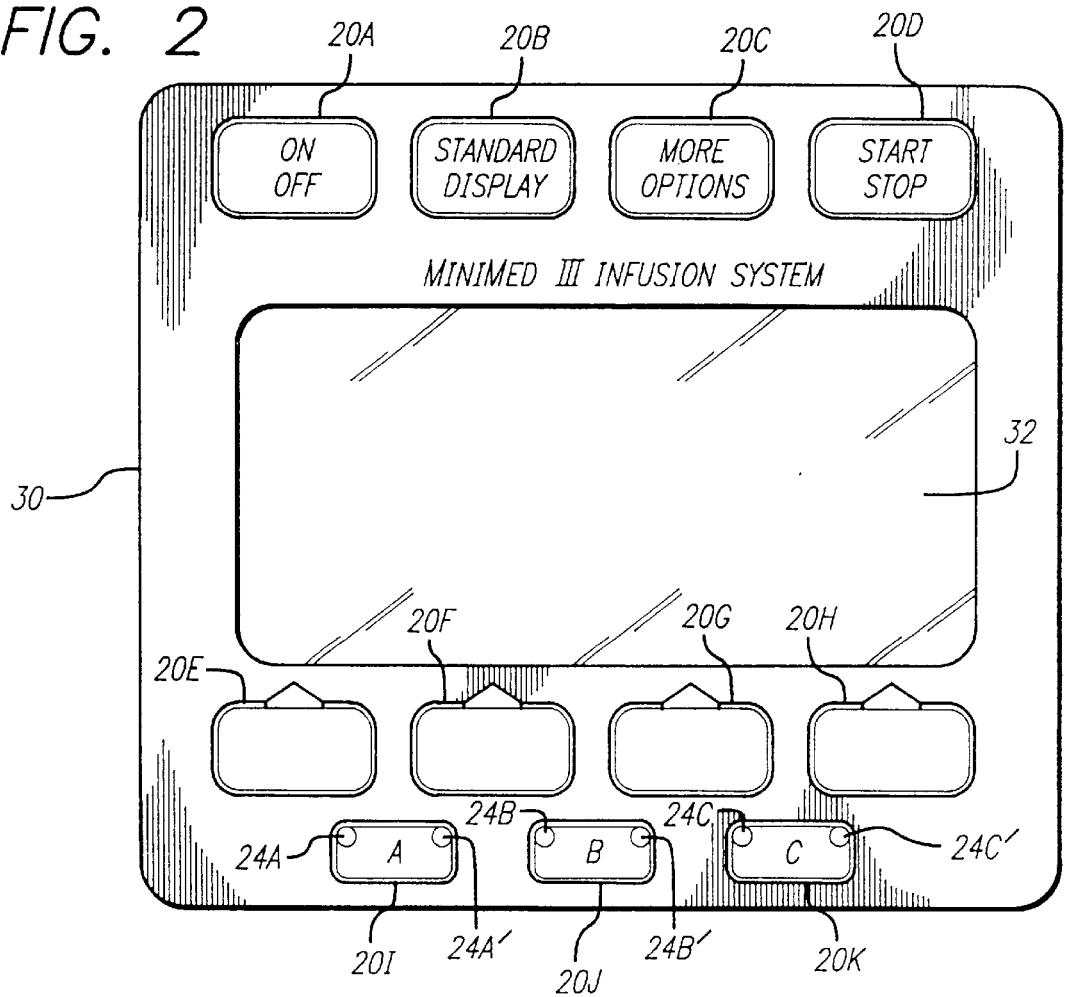
FIG. 2 is a front view of an infusion pump having a display device for providing the user interface of FIG. 1.

In a preferred embodiment the user interface 10 has four basic elements: an audio signal generator, status light-emitting diodes (LEDs), a liquid crystal display (LCD), and a plurality of user input devices. Referring to FIG. 2, a front view of the user interface hardware in the preferred embodiment is shown. A user interface chassis 30 houses a liquid crystal display 32, above which are four user input controls 20A–20D, and below which are user input controls 20E–20K. The input controls 20A–20D are momentary-contact switches labelled "ON/OFF," "STANDARD DISPLAY," "MORE OPTIONS," and "START/STOP," respectively. The switches 20E–20H located below the display 32 are so-called softkeys, whose functions depend on what is being displayed on the LCD 32. The switches 20I–20K are used to select a pump for infusion. Selecting one of these switches allows the user to access additional pages of information that are displayed on the LCD 32, providing the user with information regarding the status of the selected pump channel, or with values that may be modified by the user to program the pump channel to control the infusion provided by that channel.

The face of each pump select switch 20I–20K contains two status LEDs. Thus, pump select switch "A" 20I has status LEDs 24A and 24A' located in the upper opposing corners of the switch, pump select switch "B" 20J has status LEDs 24B and 24B' located in upper opposing corners of switch "B" 20J, and pump select switch "C" 20K has status LEDs 24C and 24C' located in the upper opposing corners of switch "C" 20K. The status LEDs 24A–24C, located in the upper left corner of the pump select switches 20I–20J when viewed by the user, emit a continuous green light when the pump is running on AC (alternating current) power when the multi-channel pumping unit is plugged into a room electrical outlet. The same status LEDs 24A–24C emit a blinking green light when the pump is running on battery power. The status LEDs 24A'–24C', located in the upper right corners of the pump switches 20I–20K when viewed by the user, emit a blinking red light when an advisory or alarm condition exists on that specific pump channel. The status LEDs 24 allow the user to make a quick visual check of the status of the instrument from a distance or in a darkened room, and the LCD 32 presents all detailed information about instrument status and operation.

Normally a user programs only one pump channel at a time when setting up an infusion regimen. The user interface 10 is designed to facilitate this by grouping information in a clinically useful way and displaying the grouping of information on the LCD 32 in a specific format referred to herein as a "page." In this manner, the pages of information are similar to pages in a book. A user may access the appropriate page of information on the display that is used for carrying out a desired task. Some tasks may require multiple pages of information, and the user interface allows the user to move between pages using the various softkeys described below. Many different types of pages are defined for the instrument. However, only those pages containing information pertinent to the dose rate calculator feature of the present invention will be described herein.

Referring now to FIG. 3, the structure of the LCD 32 and the type of information displayed in each section of the LCD 32 will be described. The LCD 32 provides the user with a display of all information and operational infusion parameters pertinent to programming and operating the pump.

The display area of LCD 32 is divided into four sections: a status line 34, a prompt line 36, a softkey area 38, and an information area 40. LCD 32 is used to display both general and detailed information about the status of the instrument, each of the pumps, and any infusion regimens. Most of this information consists of alphanumeric text. Certain other visual effects are used to enhance the readability of the display. Characters are displayed using two different fonts, as shown in FIG. 4. Normal size text is comprised of alphanumeric characters of five pixels in width by seven pixels in height. The characters are displayed in cells that are six pixels wide and ten pixels high. These characters are used for displaying the bulk of the information on the LCD 32, and are designed to be easily read from a distance of three feet.

Large size text comprises characters twice as large as normal size text, i.e. each character is fourteen pixels high by ten pixels wide. The large size text is used to display numeric data only, and is sized so that the displayed data is visible when viewed from a distance of eight to ten feet. Where a numeric value includes digits to the right of the decimal point, characters which are composed of slightly shorter, underlined digits, as shown in FIG. 4 are used to display those digits. Thus, a numeric value may be displayed using large characters to represent integer values, and slightly smaller, underlined characters representing any fractional values.

Text is normally displayed as dark pixels on a light background, but can also be displayed as reverse-contrast text, i.e., as light pixels on a dark background. When displaying a block of text in reverse-contrast, the characters always have at least one row/column of background pixels surrounding the text so that the text does not bleed to the edge of the screen. When portions of the screen blink, all such portions blink in unison. Blinking areas alternate at five-hundred millisecond intervals between the normal contents of the block and a block of the background intensity, as shown in FIG. 5.

Referring again to FIG. 3, the status line 34 of the LCD 32 is used to display the overall status of each pump. This area 34 is divided horizontally into three sub-areas 34a, 34b, and 34c, each sub-area corresponding to one of the pumps. Each of the status sub-areas 34a–34c is limited to eight characters of normal size text. The status of the selected pump is displayed in reverse-contrast text. In FIG. 3, for example, pump "A" has been selected. The possible values for text displayed in status sub-areas 34a–34c are: FAULT, indicating that the pump requires service; ALARM, indicating an alarm condition; STOPPED, indicating that the infusion regimen has stopped; INFUSING, indicating that fluid delivery is in progress; STANDBY, indicating that operation of the pump channel is suspended; and KVO, indicating that the pump is delivering fluid at a minimum rate to keep the vein open.

The prompt line 36 is located just above the softkey area 38 and is separated from it and the information area 40 by horizontal lines 42 and 44. The prompt line 36 can display a maximum of twenty-seven characters. The text displayed in the prompt line is dependent on which information page is active and what the state of the instrument is. The text displayed in the prompt line 36 is always displayed in normal size characters (FIG.4). Additionally, depending on the criticality of the prompt, certain prompts may be displayed in the prompt line 36 in reverse-contrast characters for emphasis.

The softkey area 38 includes the bottom portion of the LCD 32 and is located below the prompt line 36. Four separate sub-areas 38e–38h make up the softkey area 38, with each such sub-area centered above one of the softkeys 20E–20H. Each of the softkey sub-areas 38e–38h can display a block of text comprising up to six normal size reverse-contrast characters to represent a softkey label.

The main portion of the LCD 32 between the prompt line 36 and the status line 34 is the information area 40, which is used to display whatever information is relevant at any given time depending on the operational configuration and status of the pump. The information area 40 can display six lines of thirty-seven normal size text characters.

User inputs 20 on interface 10 consists of the front panel controls 20a–20K. The front panel controls consist of four softkeys 20E–20H and seven dedicated switches 20I–20K. Each softkey is labelled on the LCD 32 screen, immediately above the softkey, but the keys themselves are not labelled.

The "ON/OFF" control 20A allows the user to power the instrument on and off. When the instrument is "OFF," activating this control supplies the power to the instrument electronics and causes the instrument electronics to reset. When the instrument is "ON" and operating normally, activation of control 20A is sensed and results in a controlled shutdown of the instrument, ending with removal of power from the instrument after switch 20A is released. When the instrument is "ON" but a malfunction has occurred (i.e., an alarm has been indicated); activation of key 20A immediately removes power from the instrument.

Each of the pumps 18 shown schematically in FIG. 1 has a corresponding pump select key 24, as shown in FIG. 2. Each key is situated to line up with the disposable cassette for its associated pump 18. The keys 24A–24C are labelled "A, B," and "C." Activating a pump select key 24 makes the associated pump 28 the "selected" pump, and causes LCD 32 to change to the pump status page.

The "START/STOP" key 20D is used to start and stop infusion regimens. Activating key 20D toggles the infusion status of the selected pump.

The "MORE OPTIONS" key 20C is used to display more softkey functions for a particular display page. If only one set of softkey functions is available for the particular page displayed, pressing this key has no effect. When additional softkey functions are available for a particular display page, pressing the "MORE OPTIONS" key 20C cycles through the available sets of softkey functions associated with the display page, displaying each set of softkey functions in a sequential manner. If the last set of softkey functions is currently displayed and active, pressing key 20C displays and activates the first set of softkey functions in the sequence. In addition, the "MORE OPTIONS" control 20C may be used to enter a clinical configuration mode after the instrument has been turned on.

Figure 6:
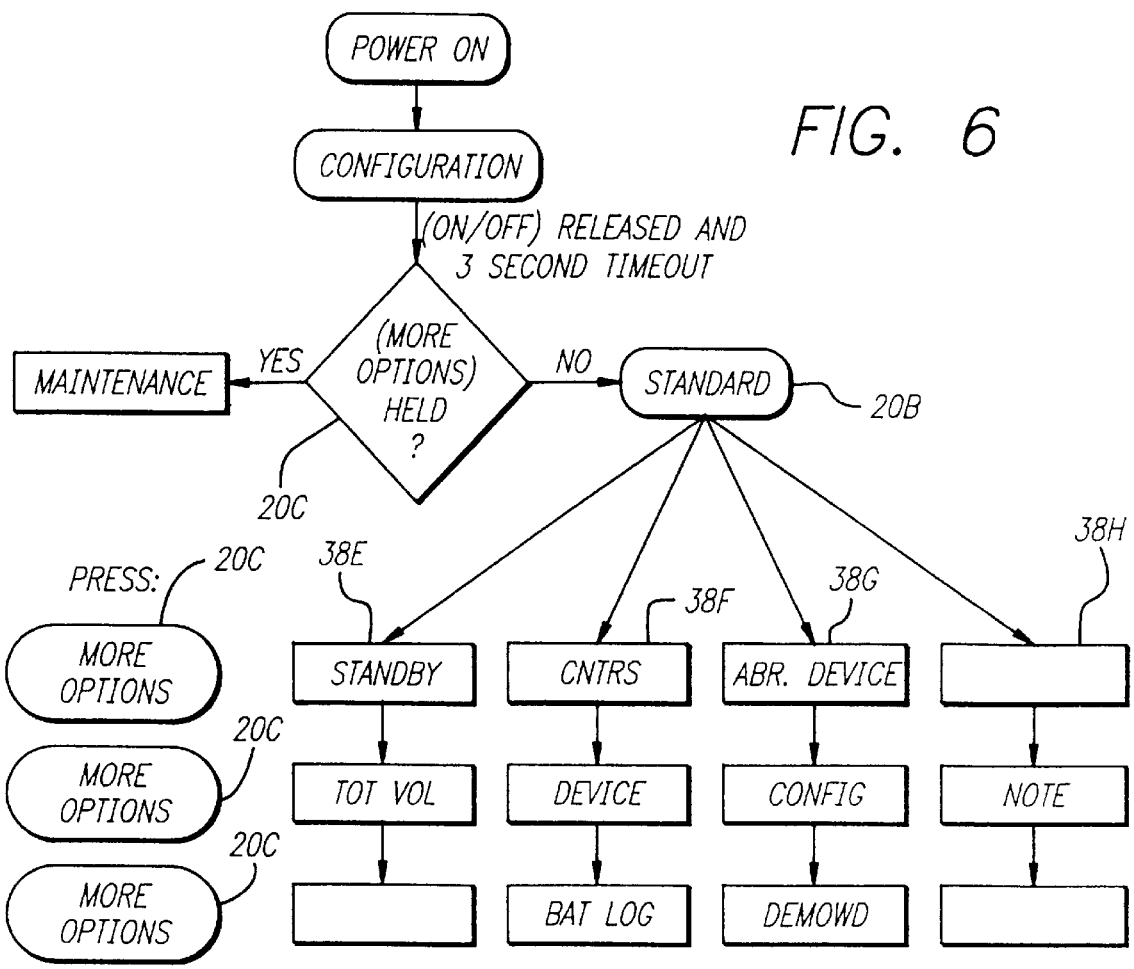
FIG. 6 is a schematic flow diagram of the overall structure of the user interface of FIG. 1, a portion of which represents the dose rate calculation feature of the present invention.

For example, the various softkeys presently available when the "MORE OPTIONS" key 20C is pressed when the standard display page is displayed on the pump are shown in FIG. 6. Pressing the "MORE OPTIONS" key 20C once results in "STANDBY" being displayed in the softkey display 38E, "CNTRS" in the softkey display 38F, and "ABR. DEVICE" in the softkey display 38G. Softkey display 38H is blank. Pressing the "MORE OPTIONS" key 20C again results in "TOT VOL" being displayed in the softkey display 38E, "DEVICE" in the softkey display 38F, "CONFIG" in the softkey display 38G and "NOTE" in the softkey display 38H. Pressing the "MORE OPTIONS" key 20C a third time causes "BAT LOG" to be displayed in the softkey display 38F and "DEMO WD" in the softkey display 38G. Softkey displays 38E, 38H are blank. Each of the softkey displays can display other messages, dependent only on the configuration and programming of the pump.

The "STANDARD DISPLAY" control 20B allows the user to return to the standard page that displays information about the status of each pump.

DESCRIPTION OF OPERATION

Entry Into Operation

When the operator releases the "ON/OFF" control, the instrument determines which operating mode should be initiated. Normally the instrument enters clinical operation, but the clinical configuration mode may be entered by pressing the "MORE OPTIONS" control before releasing "ON/OFF." When the instrument enters clinical operation, a power-up OK audio signal is given.

Turning the Instrument Off

The instrument is turned off by the operator activating the "ON/OFF" control while the instrument is "on." The following steps are taken:
 a) Fluid delivery stops for all pumps;
 b) Any memory updates are completed;
 c) All cassette homing sequence in progress are completed;
 d) All audio signals are silenced, all LED's are turned off, the LCD is blanked, and backlighting is turned off; and
 e) When "ON/OFF" is released, power to the instrument is removed and the instrument shuts down.

Pump Selection

The operator can select any of the pumps by pressing the corresponding pump select control "A," "B," or "C." Activation of one of these controls also activates the corresponding pump status page. When power is turned on, the most recently selected pump is selected. If no cassette is installed on the selected pump, the leftmost pump with a cassette installed is selected. If no pump has a cassette installed, pump "A" is selected.

Infusion Regimen Setup/Review

The operator can review the status of the three pumps by using the standard page display, which is produced by pressing the "STANDARD DISPLAY" key. All display pages reached from the standard page, either directly or indirectly, will be replaced by the standard page after a 60-second timeout if no keys are pressed by the user. Information relevant to the current infusion regimen setup is displayed for each pump.

Figure 7:
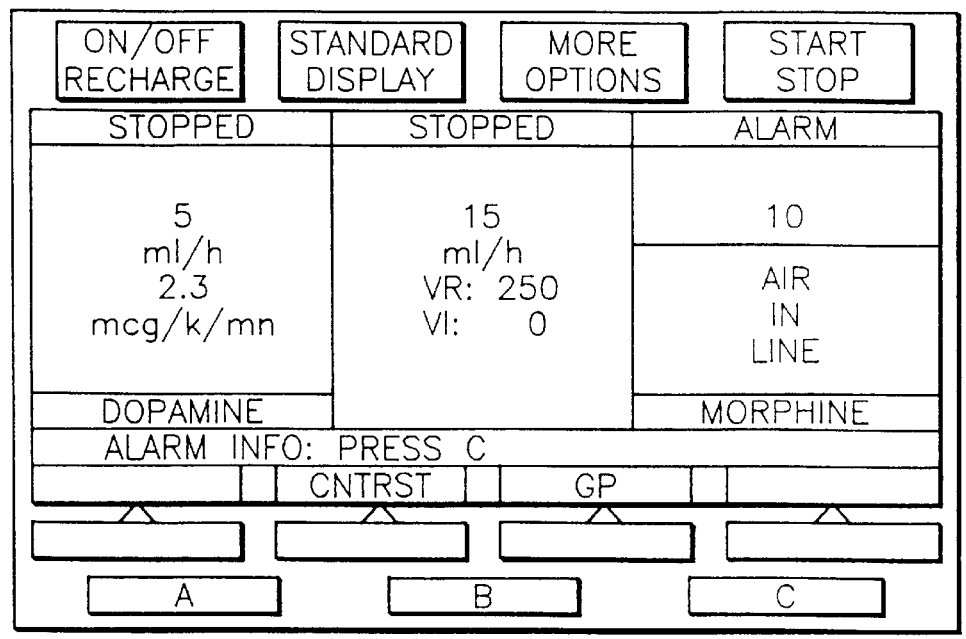
FIG. 7 is a frontal view of the display of FIG. 2 showing a representative multi-channel display of information available when the dose rate calculation feature of the present invention is enabled, and also showing a display of the information available when the dose rate calculation feature is disabled.

Referring to FIG. 7, in particular to the information displayed for the middle pump channel, the following information is displayed on the standard display page for a Rate-Volume-Time infusion.

Volumetric infusion rate (ml) is displayed in large digits. Volume remaining (ml) is displayed in normal-sized digits. Volume infused (ml) is displayed in normal-sized digits. The current device type is displayed.

When the instrument is turned on, the standard page presents the status for all pumps with a cassette in place. Mounting a cassette in the pump chassis causes the LCD 32 to display information about the corresponding pump using the standard display page. When a cassette is removed, information about that pump is displayed by the LCD 32 using the standard display page for one hundred twenty seconds and then disappears if the cassette has not been reinstalled. If another pump is selected, the information for the pump without a cassette is removed from the LCD 32.

Referring now to FIG. 8, a pump status page displayed when the pump is operating in the volumetric mode is shown. Access to this page is gained by pressing one of the pump select switches 20I–20K. The information displayed is volumetric infusion rate (ml/hr), volume remaining (ml), time remaining (hours: minutes), volume infused (ml), date and time at which volume infused was cleared, and infusion type (V/R or V/T).

Data entry softkeys available to the user include: A "SELECT" softkey to select a parameter on the display that the user wishes to change. For example, volumetric infusion rate, volume remaining, time remaining, volume infused, and infusion type may be selected. Two other softkeys are used to alter parameter values, volumetric infusion rate, volume remaining, time remaining, and infusion type. A "CLEAR" softkey is used to set the volume infused parameter to a default value. The "RECALL" key retrieves the current value of the parameter before the value was changed using the "CLEAR" or the change softkeys. Pressing the "ENTER" key enters the newly entered value for the selected parameter.

Setting Rate, Volume Remaining, and Time Remaining

Infusion regimens are commonly specified as follows:

a) The fluid is to be delivered at a specified rate. No end point for the regimen is given, i.e. no volume of fluid or infusion period, is specified.

b) A volume of fluid is to be given at a specified rate.

c) A volume of fluid is to be given over a specified length of time.

d) All the fluid in a container is to be delivered at a specified rate. ("infuse all" regimen)

To accommodate these methods of specifying an infusion regimen, and to minimize the probability of error when the operator enters the required parameters, an infusion type is set for each pump. The infusion type is either volume/rate or volume/time.

During a volume/rate type of infusion, the operator may set only the volume remaining and the infusion rate. Accepting a new value for rate or volume remaining causes the time remaining to be recalculated and displayed. If volume remaining equals "all", the time remaining is indeterminate and is displayed as "_____". If the current values of infusion rate and volume remaining specify a time remaining less than the minimal time remaining allowed, the time remaining is prefixed with the character "<." For example:

Infusion Rate : 100 ml/hr
Volume Remaining : 1 ml
Time Remaining : <00h 01m

If values for the infusion rate and the volume remaining parameters are entered in such a combination that the calculated time remaining is greater than the maximum time remaining, the time remaining is prefixed with the character ">." For example:

Infusion Rate : 1 ml/hr
Volume Remaining : 250 ml
Time Remaining : >99h 59m

During a volume/time type of infusion, the operator may set only the volume remaining and the time remaining. Accepting a new value for either the volume remaining (VR) or the time remaining (TR) parameters causes the infusion rate to be recalculated and displayed. If the operator enters a combination of values for the VR and TR parameters that specifies a rate that is out-of-range, a prompt is given when the operator attempts to accept the new value.

The operator changes between the volume/rate and the volume/time infusion types using the "SETUP" line on the pump status page. If the selected pump is currently delivering fluid this line may be selected, but the infusion type may not be changed. When the infusion type is changed, the rate, volume and time are set to default values.

Starting/Stopping Infusion Regimens

The "START/STOP" control is used to activate and suspend infusion regimens. This control directly affects only the selected pump. The exact response of the instrument to activation of this control is dependent on the status of the selected pump:

a) Stopped--pressing "START/STOP" activates the infusion regimen on the selected pump.

b) Infusion--pressing "START/STOP" suspends fluid delivery.

c) ALARM-- if a pump alarm is present on the selected pump, pressing "START/STOP" usually clears the alarm and resume fluid delivery.

d) STANDBY--pressing "START/STOP" activates the infusion regiment on the selected pump.

e) KVO--"START/STOP" stops fluid delivery and changes status to "stopped."

If the currently selected pump is inoperative, "START/STOP" has no effect.

Data Entry

When entering or changing data on the instrument, the user performs three tasks:

a) Selecting the parameter to be altered (e.g., infusion rate). This may require changing the selected pump;

b) Changing the value of the parameter (e.g., changing infusion rate from 100 ml/hr to 124 ml/hr); and c) Instructing the instrument to implement the new parameter value (e.g., "enter" the value).

In addition, a means is always available to allow the operator to cancel a change made in a parameter value before the change is implemented. There are two types of data which are required:

a) Numeric (e.g., entering infusion rate); and b) Selecting a value from a list (e.g., choosing a drug from a list of drugs for use with the drug calculator).

The following sections describe the means by which the operator can select, change, and accept parameter values for each of these types of data.

Numeric Data Entry

To select a parameter to change, the operator activates the page that contains the parameters that are to be changed. Parameters are grouped together by function and importance; a page does not contain unrelated parameters. The user then moves a cursor on the LCD 32 to highlight the parameter to be changed. Whenever a page that allows data entry is displayed, one of the parameters on the page is displayed in reverse-contrast text (highlighted). The operator moves this cursor using the "SELECT" softkey. This softkey highlights the next parameter, i.e. the cursor moves to the newly selected parameter. Pressing the "SELECT" key when the last parameter on the page is selected moves the cursor to the first parameter. Not all parameters displayed on the page may be selected; some parameters may require special actions by the operator before they can be changed.

Entry of numeric data is performed by scrolling the value of the selected parameter. When a value is to be changed, four of the softkeys function to increment and decrement the value: ↑, ↓, FAST ↑ and FAST ↓. Activating either ↑, ↓, FAST ↑ or FAST ↓ causes the number to begin to increase or decrease. If ↑ or ↓ is held down, the value increases or decreases in increasing increments. Since the range of values that parameters take is quite varied, the manner in which this acceleration occurs can be defined for each parameter. For example, when changing infusion rate, the value may initially change in one unit increments, then change in ten unit increments, then in increments of one hundred. The value stops changing when the softkey is released. If the softkey is then pressed again, the scrolling rate changes in the initial increment of one unit, not in the increments in effect when the softkey was released.

The FAST ↑ and FAST ↓ softkeys provide another method of rapidly increasing or decreasing a value. For each parameter, a list of typical values used in a health care facility are stored in a memory 23 of the pump. Pressing the FAST ↑ softkey causes the next value in the list of values to be displayed. Similarly, pressing the FAST ↓ softkey causes the next previous value in the list to be displayed. These softkeys allow the user to rapidly jump through the list of values without scrolling through the values incrementally. Once a value close to the desired value is displayed, the ↑ and ↓ softkeys can be used to select the desired value exactly, if the desired value is different from that displayed by pressing the FAST ↑ and FAST ↓ softkeys. Alternatively, the FAST ↑ and FAST ↓ softkeys may be programmed to jump to particular values within a list of values where the particular values are a part of a general list of values, but are identified either with a software flag or identifier or are contained in a look-up table or index stored in the pumps memory 23. The list of typical values, software flag or identifier, look-up table or index may be configured by a biomedical technician to customize the values available for a particular institution or clinic using the maintenance mode, which is discussed more fully below.

Once a value has been changed, the "SELECT" softkey is no longer available. Therefore a new parameter cannot be selected until the new value for the selected parameter has been canceled or accepted. Another softkey, "CLEAR," is used to reset a preset value of the volume infused parameter.

Whenever the value of the parameter is changed by pressing ↑, ↓, FAST ↑, FAST ↓ or "CLEAR" softkeys, two new softkeys are defined: the "SELECT" softkey is replaced by the "ENTER" softkey and the "CLEAR" softkey is replaced by the "RECALL" softkey. Activating the "ENTER" softkey causes the changed value currently displayed to replace the value stored in the memory 23 of the instrument with that value. The instrument then performs whatever actions are required to effect the value change. Activating the "RECALL" softkey causes the current value (the value before ↑, ↓, FAST ↑, FAST ↓ or "CLEAR" was pressed) of the selected parameter to be displayed. Activating either the "ENTER" or the "RECALL" softkeys removes the "ENTER" and "RECALL" softkey options and re-enables the "SELECT" softkey.

When a value is changed using ↑, ↓, FAST ↑ or FAST ↓, the changed value blinks (when it is not scrolling). This alerts the operator that a value has been changed but not accepted.

When changing numeric parameters, there are often other parameters that are dependent on the value of the parameter being changed (e.g. time remaining is dependent on infusion rate). When dependent parameters exist, they are always displayed on the same page as the parameters being set, and are updated accordingly when the "ENTER" softkey is pressed and the value is stored.

Selection From a List

Most parameters on the instrument have a very small number of possible values. For example, time display format is limited to "am/pm" or "24 hr" formats. To enter or change these values, the operator is allowed to choose one of the values from a list of possibilities. Two methods for entering values from a list are required: scrolling through a list and selection from a list.

Scrolling Through a List

When a list of possible values is short, and space on the LCD 32 is limited, only one value from the list is displayed at each moment. The parameter is chosen as with numeric data entry, using the "SELECT" softkey. Scrolling through the list is performed similarly to that described about, although it is possible to program the FAST ↑ and FAST ↓ softkeys so that values in the list are accessed in a desired predetermined fashion. The list and the scrolling rates can be configured using the maintenance mode to customize the selection of the parameters according to the particular needs and operation of an institution.

Selecting From a List

Once the proper selection of the list has been displayed, the operator can change the parameter value using the "SELECT" softkey. This softkey moves the cursor to the correct value on the page, wrapping around from the last to the first value on the page.

When the proper value has been selected, the operator must then accept the new value by using the "ENTER" softkey. Once the cursor has been moved to a new value in the list, the highlighted value will blink until the new value is accepted or canceled. The "SELECT" softkey used during numeric data entry should not be confused with the "SELECT" softkey used to choose a value from a list. The numeric data entry "SELECT" softkey allows the operator to select the parameter, and then the ↑ and ↓ softkeys are used to change the value. The list "SELECT" softkey is used to choose a value from a list of possibilities. The parameter to be changed has already been determined.

Operation of the Dose Rate Calculation Feature

The dose rate calculation feature of the present invention may be enabled by the operator only when the pumping channel is configured in volume-rate mode. The dose rate calculation feature must be selected for each channel individually. If the operator wishes to enter the dose rate calculation mode while the pumping channel is in the Volume-Time or secondary modes, the operator must reset the pumping channel to the volume-rate mode. Additionally, the dose rate calculation mode cannot be enabled while an infusion is in process. The pumping channel must be stopped before the dose rate calculation mode may be enabled.

The operator accesses the dose rate calculation mode of an individual pumping channel by pressing one of the keys 20I–20K assigned to the desired pumping channel. Pressing this key displays the standard display page, as is shown in FIG. 8. The operator then presses the "MORE OPTIONS" key 20C and the display changes, as illustrated by the display shown in FIG. 9, to display the "CALC ON" softkey. The operator then presses the softkey 20h below "CALC ON" to enter the dose rate calculation mode for the selected pump channel, and the DRC channel information page is displayed, an example of which is illustrated in FIG. 9.

Referring to FIGS. 8 and 9, when the DRC channel information page is displayed after the operator presses the "CALC ON" softkey, the word "DRUG?" is highlighted by reverse illumination. As described above, the parameter that is highlighted in such a manner is the parameter that can be entered or adjusted by the operator. The DRC channel information page displays variable names and entered parameters for the following parameters:

drug name, patient weight, drug concentration, drug concentration units, diluent volume for concentration, dose rate, dose amount units, dose weight units, dose time units, volumetric rate, volume remaining (VR), volume infused (VI), and dosage infused.

When the DRC channel information page is enabled, the following softkeys are displayed: "Select"; "↑"; "↓"; and "Fast ↑". As noted above, the various parameters available on the DRC channel information page are accessed sequentially by pressing the "Select" softkey until the desired parameter is highlighted. In general, once the operator has chosen the parameter to be changed by pressing "Select", the value of the parameter is changed by pressing either the ↑ or ↓ softkeys. The ↑ softkey is used to scroll up from the lowest value to the highest value of a list of available values for the parameter. Conversely, the ↓ softkey is used to scroll down from the highest to the lowest value in the list of values. The ↑ and ↓ will continue to scroll through the list of values if the key is held down. Additionally, when selecting a drug name from the list of drug names, the list will wrap around if the softkeys are pressed when the value displayed is at either the top of the list or the bottom of the list. Thus, for example, if the value displayed after pressing the ↑ softkey is the first drug name in the list, pressing the ↓ softkey again will display the last drug name in the list.

As described above, when the DRC channel information page is first enabled, the "DRUG?" parameter is highlighted by default. The drug names are stored in a list which may, but not necessarily, be arranged alphabetically in ascending order from A to Z. The list of drugs is fixed, and cannot be changed by a technician without changing the program stored in the memory 23 of the pump. The operator scrolls through the drug name list by pressing the ↑ or ↓ softkeys. In DRC mode, the FAST ↑ and FAST ↓ softkeys are programmed to jump to a predetermined name, for example, the softkey may be programmed to display the first drug name in each set of drug names beginning with a letter of the alphabet. For example, the first drug name beginning with A, B or C and so forth. As the operator scrolls through the list of drug names, each name is displayed on the DRC channel information page. As each drug name is displayed while the list is being scrolled, the drug concentration units and dose rate units programmed for that particular drug name are automatically displayed on the DRC channel information page. When the desired drug has been selected from the list of drug names, the operator may press the "ENTER" softkey to lock in the drug name and automatically move to the Patient Weight parameter on the DRC channel information page.

In many institutions, a small number of drugs are routinely prescribed within specified narrow ranges of drug concentrations units and dose rate units. The pumping system of the present invention therefore provides a rapid method of selecting these drugs using the "FAST ↑" and "FAST ↓" softkeys. Using these softkeys, an operator may rapidly scroll through the list of drug names; as discussed above, the FAST ↑ and FAST ↓ softkeys may be programmed by a biomedical technician using the maintenance mode to customize the operation of the pump for a particular institution or clinical setting.

Selecting a drug name from the list of drug names sets the following parameters for infusion of the drug: the standard dose rate units for that drug, standard concentration units for the drug concentration, the patient weight, dose rate, and volumetric rate are cleared to "- - - ", and the drug concentration amount and diluent volume are cleared to "- - - ". All parameters may be changed by the operator after selecting a drug name from either the standard list or the abbreviated list except the drug concentration units and the dose rate units.

At times a drug will be prescribed that is not contained in either the drug name list or the abbreviated drug name list because it is a new drug or one that is not routinely used in the institution. In this case, the operator may still use the dose rate calculation feature of the infusion pump by entering values for the infusion parameters when the "DRUG?" parameter is selected. Selecting the drug name "DRUG?" allows the operator to enter values for each of the parameters displayed on the DRC channel information page. When the drug name selected is "DRUG?", the patient weight, the dose rate, and volumetric rate will be cleared to "- - - ", the volume remaining will be cleared to "1 ml," the volume infused and dose infused will be cleared to "0."

Many drugs are prescribed so that the patient is given a specific amount of the drug based on the patient's weight. When a drug is selected from either the standard list or the abbreviated list of drug names that requires the patient's weight, the "Weight" parameter will display "- - - " and infusion will not be able to start until a value has been entered. If a drug is selected whose delivery is not based on the patient's weight, the line on the DRC channel information page that displays the patient weight will be replaced by a blank line. The operator will be required to provide a value for the patient's weight if the dose rate units for the selected drug is, for example, one of the following: mcg/kg/min; mcg/kg/hr; mg/kg/day. Many other possible combinations are possible; the units presently being used are listed in the Appendix.

The operator may enter a value for the patient's weight by first selecting the "Weight" parameter by pressing the "SELECT" softkey until the "Weight" parameter is highlighted in the display. When the patient's weight is entered when the value displayed is "- - - ", pressing the ↑, ↓, or FAST ↑ softkeys will change the value to 70 KG for adult device types and 1 KG for Neonatal device types. The patient's weight may be entered either in kilograms (KG) or grams (G). The equivalent weight in pounds (lbs) will be automatically calculated and displayed. The patients weight may also be entered in pounds; thus the patient's weight will be automatically displayed in kilograms or grams. The patient's weights are entered by using the ↑, ↓, FAST ↑ and FAST ↓ softkeys to increment or decrement the value displayed on the DRC channel information page until the desired weight is displayed. Changing the patient's weight will always result in the volumetric rate being recalculated and displayed.

The drug concentration to be infused is calculated based on the values of the drug amount and diluent volume parameters. As described above, selecting a drug name from the standard list of drug names automatically enters default values for the concentration units. The operator must then enter values for the drug amount and the diluent volume by selecting the parameters using the "SELECT" softkey and then scrolling through allowable values of the parameters using the ↑, ↓, FAST ↑ and FAST ↓ softkeys to increment or decrement the value displayed on the DRC channel information page until the desired value is displayed. When either the drug concentration, drug concentration units or diluent volume is changed, the volumetric rate is automatically recalculated and displayed. Additionally, changing the diluent volume results automatically sets the value of the volume to be infused parameter to equal the value selected for the diluent volume.

When the operator enters values for drugs not listed on either the standard or abbreviated drug name lists, but instead uses the generic "DRUG?" value, the operator may also change the drug concentration units. The following is a list of drug amount units available for selection by the operator: micrograms (mcg), milligrams (MG), grams (G), milliequivalents (Meq), Units (Un), milliunits (MUn) and millimoles (Mmol). The diluent volumes are entered in milliliters (ml). When a drug name is selected from the standard or abbreviated drug lists, however, the drug concentration units are automatically set and cannot be changed.

The dose rate units displayed on the DRC channel information page are comprised of the drug concentration units, the patient body weight units, and the infusion time units. The dose rate units may be changed by the operator only if the drug name selected is "DRUG?". Otherwise, the dose rate units are automatically set when a drug name is selected from either the standard drug name list or the abbreviated drug name list. The dose rate units are changed by selecting and scrolling each portion of the unit separately, that is, each of the units for drug concentration, patient body weight, and infusion time must be separately selected and set by the operator. The operator first presses the "SELECT" softkey until the first portion of the dose rate units, the drug amount unit, is highlighted. After scrolling through the stored list of values for the drug amount units until the desired unit is displayed, the operator presses the "SELECT" softkey to move the highlight bar in the display to the patient weight unit parameter. The patient weight unit is selected as described above, and the selection process repeated for the infusion time unit parameter.

The actual dose rate desired to be infused may also be entered by the operator by pressing the "SELECT" softkey until the value for the dose rate, which may be either a numeric value if previously entered, or "- - - " is not previously entered, is highlighted in the DRC channel information page display. The operator may then scroll through a list of allowable numeric values for the dose rate until the value for the desired dose rate is displayed. The dose rate to be used is confirmed by the operator by then pressing "ENTER." When the dose rate is changed the volumetric rate is automatically recalculated and displayed. If the entered value of the dose rate results in a volumetric rate that is outside the allowable range for the drug or the pump configuration, the volumetric rate is set to a value of "- - - " and infusion cannot be started until a dose rate is selected that results in a valid volumetric rate.

The volumetric rate is displayed on the DRC channel information page and can be changed from this page using the ↑ and ↓ softkeys to scroll through a list of allowable values for the volumetric rate. If the operator changes the volumetric rate, the dose rate is automatically recalculated. Additionally, the volumetric rate is recalculated and displayed if the operator changes the values for the patient weight, drug concentration, including drug amount, drug amount units, and diluent volume, the dose rate or dose rate units, or the drug name. When a new drug name is selected from either the standard list of drug names or the abbreviated list of drug names the value of the volumetric rate is cleared to display the value "- - - ". If any of the above listed parameters are changed resulting in a recalculated value of the volumetric rate that is outside of an allowable range, either for the drug to be infused or for the selected configuration of the pump, the volumetric rate will be set to the value "- - - " and infusion will not be allowed to begin until a valid volumetric rate is displayed.

The volume remaining to be infused is displayed on the DRC channel information page, and may be changed from this page. When the diluent volume is changed, the volume remaining is automatically set to the same value as the value for the diluent parameter. The value of this parameter may changed while infusing, to be discussed below.

The final line of the DRC channel information page displays the volume infused and dose infused parameters. These values are dependent upon the operation of the infusion pump, and may not be changed from the DRC channel information page; the values of the volume infused and dose infused parameters may only be cleared from the DRC channel information page. While the values displayed for the volume infused and dose infused parameters are related, they may be cleared independently of each other. Volume infused is displayed in milliliters and the dose infused is displayed in the same units as the drug concentration. If the drug concentration units are changed, the value for the dose infused parameter is automatically set to "0".

Once the operator has selected values for all the necessary parameters to his or her satisfaction, infusion may be started by pressing the "START/STOP" key 20d. If the selected value of any of the parameters results in a volumetric rate that is outside the allowable range for the drug or pump configuration, the volumetric rate will be displayed as "- - - " and infusion will not be allowed to start. The prompt line 36 will display a message to the operator such as "Rate too high; Reenter Value" or "Rate too low; Reenter Value" if the pump is infusing. If the pump is stopped, the prompt line 36 will display the message "Verify all dose settings" to the operator. The operator may also switch to the standard display page by pressing the "STANDARD DISPLAY" key 20B.

Referring now to FIG. 7, the standard display page is shown with channel A and channel C having the dose rate calculation feature enabled, and with channel B set up without enabling the dose rate calculation feature. As illustrated by the display for channel A, when the dose rate calculation feature is enabled, the standard display page displays the infusion rate, in this example, 5 ml/h, the dose rate, here 2.3 mcg/k/mn, and the drug name, for example, Dopamine. In contrast, when the dose rate calculation is not enabled, as for channel B, the standard display page displays the volumetric rate, 15 ml/h, the volume remaining (VR), 250, and the volume infused (VI), 0. When an alarm condition is detected by the infusion system, as is depicted for channel C, the drug name remains displayed to indicate that the dose rate calculation feature is enabled, but the status line area 34c for channel C displays "Alarm" and the type of alarm, here "Air in Line" is displayed. The volumetric rate is also displayed, but without the volumetric units being displayed.

Operation of the Dose Rate Calculation Feature While Infusing

The dose rate calculation feature may not be enabled during infusion of standard volume-rate, volume-time, or secondary modes. The DRC channel information page may be accessed, however, during infusion if the dose rate calculation feature is already enabled. Thus, the dose rate calculation feature may be used to titrate the dosage of the drug being infused into the patient. This feature is especially useful when the infusion is to go on for a long period of time, and the dosage may be adjusted depending on the vital signs of the patient to accomplish improved therapeutic results. The DRC channel information page can be accessed by the operator by pressing the desired channel key 20I–20K while the pump is infusing.

While the pump is infusing, the operator may change the following parameters without stopping the infusion: dose rate, volumetric rate and volume remaining. The values for the volume infused and dose infused may be cleared to a value of "0", but they may not be changed. If the operator changes the dose rate, the volumetric rate is automatically recalculated. Conversely, changing the volumetric rate results in the automatic recalculation and display of the dose rate. Accessing the DRC channel information page while the pump is infusing results in the dose rate parameter being highlighted when the DRC channel information page is displayed.

If the selected value of any of the parameters changed while the pump is infusing results in a volumetric rate that is outside the allowable range for the configuration of the pump, the operator will be prompted by a message displayed in the prompt line 36 of the DRC channel information page display such as "Rate too high; Reenter Value", if the volumetric rate is higher than the maximum allowable value, or "Rate too low; Reenter Value" if the volumetric rate is lower than the minimum allowed value, and, "Press Enter or Recall." The infusion will continue at the previously selected volumetric rate until the operator changes the parameters necessary to result in a calculated volumetric rate that is within the allowable range for the drug or pump configuration.

The dose rate calculation feature may be disabled by pressing the "START/STOP" key 20d while the pump is infusing to stop the infusion. The "MORE OPTIONS" key 20C is then pressed to display the additional softkeys. The operator may then press the "CALC OFF" softkey 20h to disable the dose rate calculation feature. When the "CALC OFF" softkey is pressed, the values selected for the drug name, patient weight, drug concentration and dose rate will be cleared and set to their default values as described above. The dose rate calculation feature may also be disabled by pressing the "ON/OFF" key 20A to turn off power to the infusion system. If the system is turned off for less than five minutes, all values for the parameters selected and displayed on the DRC channel information page will be retained. However, if the system is turned off for more than five minutes, all parameter values except the values for the volumetric rate, the volume remaining and volume infused will be deleted and the dose rate calculation feature disabled.

Configuration of the Dose Rate Calculation List

Because the instrument is capable of operating in a wide range of environments, performing extremely sophisticated functions, it is necessary to configure the operation of the instrument to the environment to which it is to be used. Configuration functions must be performed when the instrument is not being used to infuse fluids into a patient. Therefore, these functions are not available during normal operation and require special procedures in order to be accessed.

Instrument configuration involves changing fairly sensitive information in the instrument, and is expected to be performed only in the biomedical engineering department of the institution. Among the parameters and features that may be altered are the lists of drug names and their associated groups of infusion parameters. The pump may be provided to the institution with a preprogrammed list of drug names and groups of associated infusion parameters, or the pump may be supplied with no programming, allowing easy customization by qualified personnel to meet the requirements of the various departments within the institution. For example, a single drug may be used in different ways by different departments, and thus the pump may be individually programmed so that different groups of infusion parameters are chosen when the drug name is selected from the list of drug names. Furthermore, this feature allows the qualified personnel to add, remove and update the list of drug names, as well as the associated infusion parameters.

In operation, the memory 23 of the pumping system is updated by first preparing files containing the parameters to be stored in the pump using the computer 12 running specialized software 16. When the file containing the desired information is ready, the pumping system is connected to the computer 12 by way of the communications interface 14.

The pumping system is then put into "Maintenance Mode" to enable the pumping system to receive the contents of the file from the computer 12 via the communications interface 14. This is accomplished by turning the pump off by pressing the "ON/OFF" control 20A to power down the pump if it is already in a powered state. The "ON/OFF" control 20A is then pushed again to power up the pump. While the pump is powering up, the maintenance mode is enabled by pressing and holding the "MORE OPTIONS" control 20C. A communications session between the instrument and the computer 12 running the specialized software 16 is initiated via the interface 14.

While in the maintenance mode, "Maintenance" is displayed on the status line 34 of the display 32. No softkeys are available. Maintenance mode is terminated by pressing the "ON/OFF" control 20C to power the instrument down.

When the maintenance page has been accessed, the qualified person downloads the file containing the list of drug names and their associated infusion parameters to the instrument via the interface 14. Downloading of the file is initiated by the computer 12 sending a download command, to which the instruments responds by sending a "Ready" command via the communications interface 14. When the "Ready" command is received by the computer 12, the specialized software 16 begins sending the contents of the file to the instrument via the communications interface 14. When the last portion of the file has been transferred, the computer 12 completes the file transfer by sending a "Complete" message to the instrument via the communications interface 14. The instrument then responds by sending a "Ready" message to the computer 12. If no errors have occurred, the memory of the instrument now contains the contents of the downloaded file, and the maintenance mode is exited as described above. The next time that an operator attempts to select a drug name from the displayed list of drug names, the list displayed will be the altered list provided to the instrument by the computer 12, and the infusion parameters selected by selecting one of the drug names will be the altered values stored in the instruments memory 23 during the downloading procedure described. The contents of the instrument memory 23 will remain unchanged until the next maintenance session.

While several forms of the invention have been illustrated and described, it will also be apparent that various modifications can be made without departing form the spirit and scope of the invention. Accordingly, it is not intended that the invention be limited, except by the appended claims.

What is claimed:

1. An infusion system for infusing medical fluid to a patient, comprising;
   a pump for infusing the medical fluid;
   a memory for storing a plurality of infusion parameters for controlling the operation of the pump, the memory also having stored within it flags associated with a plurality of selected stored memory data;
   a display;
   a selection key that provides a selection signal when actuated;
   a fast selection key that provides a fast signal when actuated; and
   a processor responsive to the selection signal to select and retrieve infusion parameters from the entire plurality of parameters stored in the memory, to display selected parameters and to control the pump to operate in accordance with the selected parameters, and also responsive to the fast signal to select among only the flagged memory data, to display selected flagged memory data and to control the pump to operate in accordance with the selected flagged memory data.

2. The system of claim 1, wherein the memory has stored within it a plurality of identifying names, each of which is associated with a group of stored infusion parameters and wherein the flagged memory data comprises a plurality of selected ones of the identifying names, the plurality of selected ones being less than the entire plurality of stored names; and
   the processor is responsive to the fast signal to select among only the flagged identifying names stored in the memory, to display the selected group of parameters associated with the selected identifying name and to control the pump to operated in accordance with the group of parameters associated with the selected identifying name.

3. The system of claim 2, wherein the identifying name comprises a drug name.

4. The system of claim 2, further comprising a remote programming source being capable of providing data comprising identifying names; and a communications interface for connecting the remote programming source to the memory and for transmitting the data from the remote programming source to the memory for storage in the memory.

5. The system of claim 4, wherein the identifying name comprises a drug name.

6. The system of claim 2, wherein
   the memory has stored within it a plurality of values associated with at least some of the infusion parameters, and the flagged memory data further comprises a plurality of selected ones of the stored values, the plurality of selected ones being less than the plurality of stored values; and
   wherein the first selection key is actuated to select one infusion parameter from among the plurality of infusion parameters, the processor is responsive to the fast signal to select among only the flagged values stored in the memory for the selected infusion parameter, to display the selected flagged value, and to control the pump to operate in accordance with the selected flagged value.

7. The system of claim 2, wherein the flags are associated with identifying names comprising the names of drugs more commonly used with the pump.

8. The system of claim 2, wherein each group of stored infusion parameters associated with its respective identifying name includes dosage units and concentration units.

9. The system of claim 1, wherein the memory has stored within it a plurality of values associated with at least some of the infusion parameters; the flagged memory data further comprises a plurality of selected ones of the stored values, the plurality of selected ones being less than the entire plurality of stored values; and
   wherein the selection key is actuated to select an infusion parameter from among the entire plurality of infusion parameters, the processor is responsive to the fast signal to select among only the flagged values stored in the memory for the selected infusion parameter, to display the selected flagged value, and to control the pump to operate in accordance with the selected flagged value.

10. The system of claim 9, wherein the flag is associated with values of infusion parameters comprising values of infusion parameters more commonly used with the pump.

11. The system of claim 9, further comprising:
    a remote programming source being capable of providing data comprising values associated with infusion parameters; and
    a communications interface for connecting the remote programming source to the memory and for transmitting the data from the remote programming source to the memory for storage in the memory.

12. The system of claim 6, further comprising:
    a remote programming source being capable of providing data comprising identifying names and values associated with infusion parameters; and
    a communications interface for connecting the remote programming source to the memory and for transmitting the data from the remote programming source to the memory for storage in the memory.

13. The system of claim 6, wherein the flags are associated with values of infusion parameters comprising values of infusion parameters more commonly used with the pump.

14. The system of claim 6, wherein the flags are associated with identifying names comprising the names of drugs more commonly used with the pump.

15. The system of claim 12, wherein the identifying name comprises a drug name.

16. The system of claim 13, wherein the identifying name comprises a drug name.

17. The system of claim 13, wherein a second flag is associated with identifying names comprising the names of drugs more commonly used with the pump.

18. An infusion system for infusing medical fluid to a patient, comprising;
   a pump for infusing the medical fluid;
   a memory for storing a plurality of infusion parameters for controlling the operation of the pump, the memory also having stored within it flags associated with identifying names comprising names of drugs more commonly used with the pump, the flags also associated with a plurality of selected stored memory data;
   a display;
   a selection key that provides a selection signal when actuated
   a fast selection key that provides a fast signal when actuated; and
   a processor responsive to the selection signal to select and retrieve infusion parameters from the entire plurality of parameters stored in the memory, to display selected parameters and to control the pump to operate in accordance with the selected parameters, and also responsive to the fast signal to select among only the flagged memory data, to display selected flagged memory data and to control the pump to operate in accordance with the selected flagged memory data;
   a remote programming source being capable of providing data comprising identifying names; and
   a communications interface for connecting the remote programming source to the memory and for transmitting the data from the remote programming source to the memory for storage in the memory.

19. An infusion system for infusing medical fluid to a patient, comprising;
   a pump for infusing the medical fluid;
   a memory for storing a plurality of infusion parameters for controlling the operation of the pump, the memory also having stored within it flags associated with selected memory data comprising values of infusion parameters more commonly used with the pump;
   a display;
   a selection key that provides a selection signal when actuated;
   a fast selection key that provides a fast signal when actuated; and
   a processor responsive to the selection signal to select and retrieve infusion parameters from the entire plurality of parameters stored in the memory, to display selected parameters and to control the pump to operate in accordance with the selected parameters, and also responsive to the fast signal to select among only the flagged memory data, to display selected flagged memory data and to control the pump to operate in accordance with the selected flagged memory data;
   a remote programming source being capable of providing data comprising values associated with infusion parameters; and
   a communications interface for connecting the remote programming source to the memory and for transmitting the data from the remote programming source to the memory for storage in the memory.

20. A method of infusing medical fluid to a patient with a pump having a memory having stored within it a plurality of infusion parameters for controlling the operation of the pump, a display, a selection key that provides selections signals when actuated, and a processor responsive to selection signals to select and retrieve infusion parameters from the entire plurality of parameters stored in the memory, to display the selected parameters and to control the pump to operate in accordance with the selected parameters, the method comprising the steps of:
   storing in the memory flags associated with a plurality of selected stored memory data;
   providing a fast signal from a fast selection key when the fast selection key is actuated; and
   selecting among only the flagged memory data, displaying selected flagged memory data and controlling the pump to operate in accordance with the selected flagged memory data in response to the fast signal.

21. The method of claim 20, further comprising the steps of:
   storing in the memory a plurality of identifying names associated with at least some of the infusion parameters;
   storing and associating the flags with a plurality of selected ones of the identifying names, the plurality of selected ones being less than the entire plurality of stored names; and
   selecting among the flagged identifying names stored in the memory in response to the fast signal, displaying the selected parameters associated with the selected identifying name and controlling the pump to operate in accordance with the parameters associated with the selected identifying name.

22. The method of claim 20, further comprising the steps of:
   storing in the memory a plurality of values associated with at least some of the infusion parameters;
   storing and associating the flags with a plurality of selected ones of the values, the plurality of selected ones being less than the entire plurality of stored names; and
   selecting among only the flagged values stored in the memory in response to the fast signal, displaying the selected flagged value, and controlling the pump to operate in accordance with the selected flagged value in response to the fast signal.

23. The method of claim 21, further comprising the steps of:
   storing in the memory a plurality of values associated with at least some of the infusion parameters;
   storing and associating second flags with a plurality of selected ones of the values, the plurality of selected ones being less than the entire plurality of stored names; and
   selecting among only the second flagged values stored in the memory in response to the fast signal, displaying the selected second flagged value, and controlling the pump to operate in accordance with the selected second flagged value in response to the fast signal.

24. The method of claim 21, further comprising the step of associating the identifying name with a drug name.

25. The method of claim 21, further comprising the step of associating the flags with identifying names comprising the names of drugs more commonly used with the pump.

26. The method of claim 21, further comprising the step of associating dosage units and concentration units with the selected infusion parameters and with its respective identifying name.

27. The method of claim 21, further comprising the steps of:

provide a remote programming source capable of providing data comprising identifying names;

connecting the remote programming source to the memory with a communications interface; and transmitting the data from the remote programming source to the memory for storage in the memory.

28. The method of claim 22, further comprising the step of associating the flags with values comprising the values of infusion parameters more commonly used with the pump.

29. The method of claim 22, further comprising the steps of:

providing a remote programming source capable of providing data comprising values associated with infusion parameters;

connecting the remote programming source to the memory with a communications interface; and transmitting the data from the remote programming source to the memory for storage in the memory.

30. The method of claim 23, further comprising the step of associating the identifying name with a drug name.

31. The method of claim 23, further comprising the step of associating the flags with identifying names comprising the names of drugs more commonly used with the pump.

32. The method of claim 23, further comprising the step of associating dosage units and concentration units with each group of infusion parameters and with its respective identifying name.

33. The method of claim 23, further comprising the steps of:

providing a remote programming source capable of providing data comprising identifying names and values associated with infusion parameters;

connecting the remote programming source to the memory with a communications interface; and transmitting the data from the remote programming source to the memory for storage in the memory.

\* \* \* \* \*